(12) United States Patent
Knierim

(10) Patent No.: US 12,404,955 B2
(45) Date of Patent: Sep. 2, 2025

(54) RADIAL SEAL WITH MINIMAL DEAD SPACE

(71) Applicant: B. Braun Avitum AG, Melsungen (DE)

(72) Inventor: Michael Knierim, Melsungen-Schwarzenberg (DE)

(73) Assignee: B. Braun Avitum AG, Melsungen (DE)

( * ) Notice: Subject to any disclaimer, the term of this patent is extended or adjusted under 35 U.S.C. 154(b) by 9 days.

(21) Appl. No.: 18/475,689

(22) Filed: Sep. 27, 2023

(65) Prior Publication Data

US 2024/0110649 A1 Apr. 4, 2024

(30) Foreign Application Priority Data

Sep. 30, 2022 (DE) .................... 10 2022 125 309.0

(51) Int. Cl.
*F16L 19/02* (2006.01)

(52) U.S. Cl.
CPC ............................... *F16L 19/0212* (2013.01)

(58) Field of Classification Search
CPC ... F16L 19/0212; F16L 19/0218; F16L 17/00; F16L 17/02; F16L 17/06; F16L 21/02; F16L 21/03; F16L 21/035; F16L 21/05; F16L 25/10; F16L 27/08; F16L 27/0804; F16L 47/06; F16L 47/065; F16L 47/08;
(Continued)

(56) References Cited

U.S. PATENT DOCUMENTS

| | | | | |
|---|---|---|---|---|
| 4,398,726 A | * | 8/1983 | Heisler | F16L 47/065 285/915 |
| 4,905,766 A | * | 3/1990 | Dietz | F16L 47/24 285/239 |

(Continued)

FOREIGN PATENT DOCUMENTS

| | | |
|---|---|---|
| AU | 2011292047 B2 | 1/2016 |
| CN | 202834069 U | 3/2013 |

(Continued)

OTHER PUBLICATIONS

Search Report received in German Application No. 10 2022 125 309.0 dated Jun. 7, 2023, with translation, 39 pages.

(Continued)

*Primary Examiner* — Aaron M Dunwoody
(74) *Attorney, Agent, or Firm* — Christopher A. Rothe; CM Law

(57) ABSTRACT

A medical connector link for establishing a fluid connection between two fluid lines includes a first male link element/connector element and a second female link element/connector element. The male link element is arranged or arrangeable in the female link element such that a fluid passage of the male link element and a fluid passage of the female link element form a common fluid passage. The connector link further includes a seal element arranged within a circumferential groove on an outer side of the male link element or on an inner side of the female link element. The seal element seals a radial gap between the female link element and the male link element. The male link element and/or the female link element have at least one recess that fluidically connects the common fluid passage with the circumferential groove.

15 Claims, 2 Drawing Sheets

(58) Field of Classification Search
CPC .. F16L 2201/40; F16L 2201/44; A61M 39/10; A61M 39/16; A61M 39/14
See application file for complete search history.

(56) References Cited

U.S. PATENT DOCUMENTS

| | | | |
|---|---|---|---|
| 5,058,907 A | | 10/1991 | Percebois et al. |
| 5,395,139 A | * | 3/1995 | Morrisson ............... F16L 41/03 285/330 |
| 2002/0171243 A1 | | 11/2002 | Jost |

FOREIGN PATENT DOCUMENTS

| | | |
|---|---|---|
| CN | 103140258 A | 6/2013 |
| DE | 2855646 A1 | 6/1980 |
| DE | 19628551 B4 | 4/2004 |
| EP | 0406144 A1 | 1/1991 |
| EP | 1574774 B1 | 6/2007 |
| GB | 2000240 A | 1/1979 |
| WO | 0188424 A1 | 11/2001 |

OTHER PUBLICATIONS

Search Report received in European Application No. 23198704.1-1015 dated Jan. 26, 2024, with translation, 12 pages.

* cited by examiner

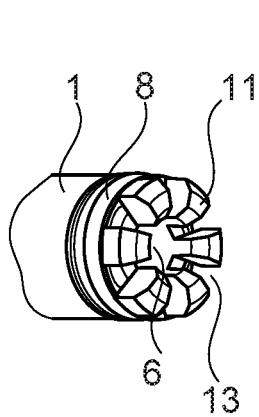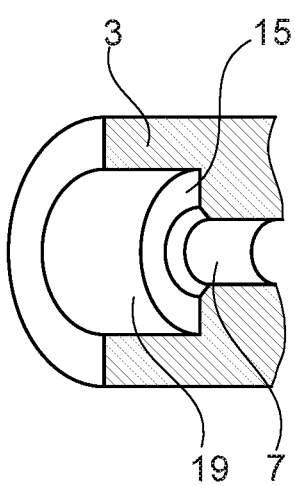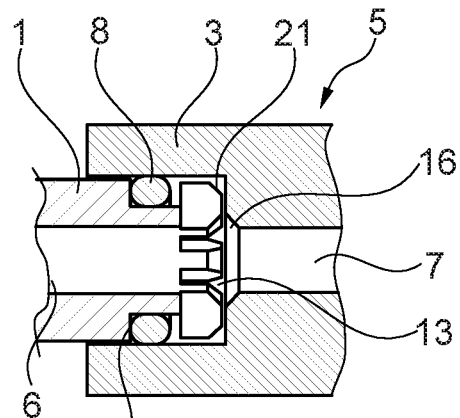
Fig. 1A  Fig. 1B  Fig. 1C
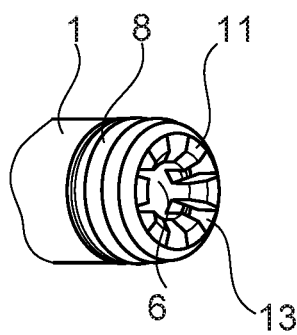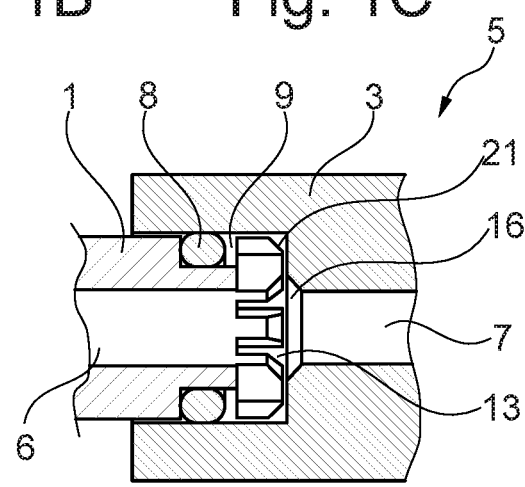
Fig. 2A  Fig. 2B
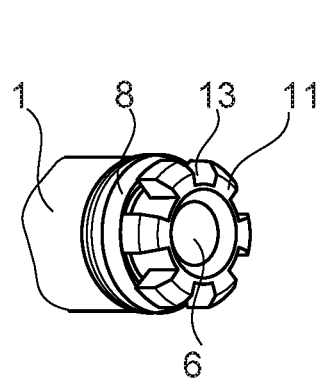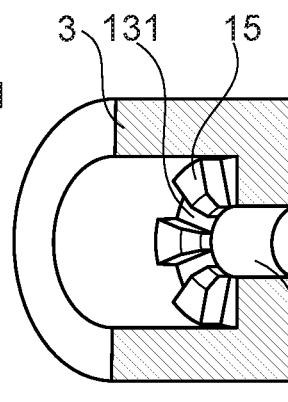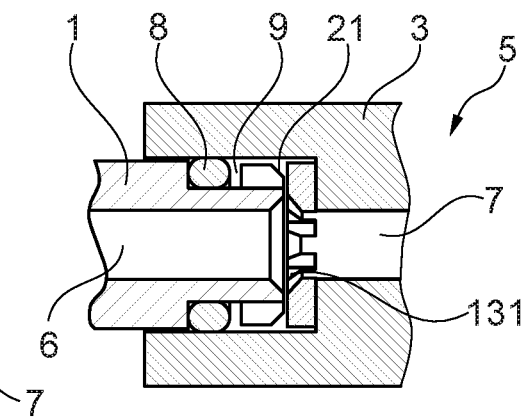
Fig. 3A  Fig. 3B  Fig. 3C

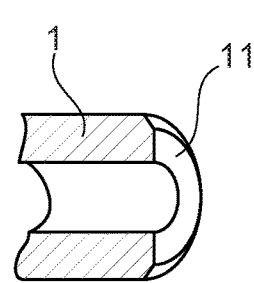 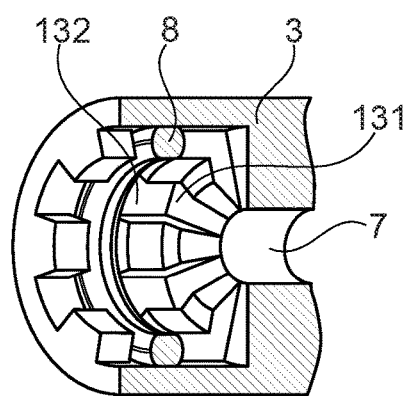 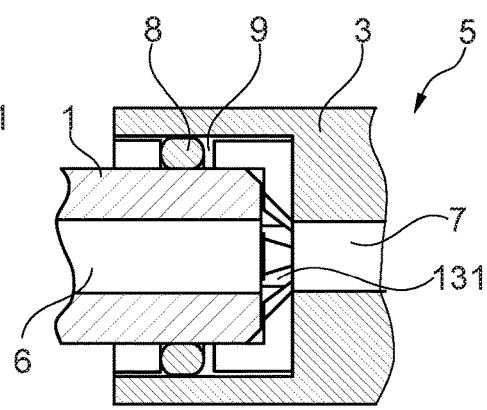
Fig. 4A     Fig. 4B     Fig. 4C
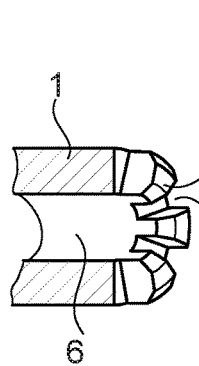 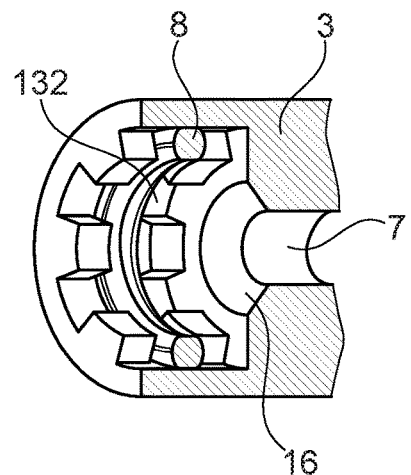 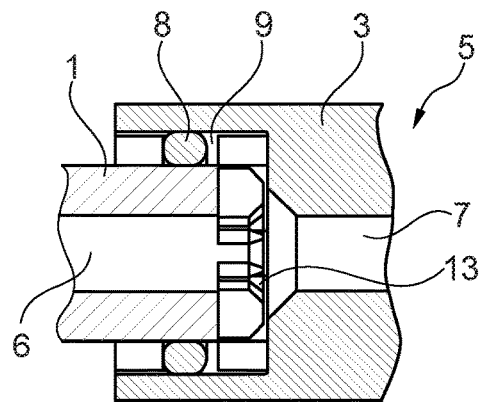
Fig. 5A     Fig. 5B     Fig. 5C

RADIAL SEAL WITH MINIMAL DEAD SPACE

CROSS-REFERENCE TO RELATED APPLICATION(S)

This application claims priority under 35 U.S.C. § 119 to German Application No. 10 2022 125 309.0, filed Sep. 30, 2022, the content of which is incorporated by reference herein in its entirety.

FIELD

The present disclosure relates to a radial seal with minimal dead space, particularly for a medical connector link having a male link element, a female link element, and a radial seal element.

BACKGROUND

Connector links with a first link element arranged in a second link element are well known. Pinion-cylinder systems with an (axially movable) pinion or rod and a cylinder housing are well known and usually have a radial seal element, preferably in the form of a sealing ring, which is formed as a pinion seal on the first link element or as a rod seal on the second link element. The object of this seal element is to prevent the ingress or leakage of fluid through the radial gap/crack between the first link element and the second link element. Conventionally, this seal element is arranged within a radial groove, which is formed in such a way that sufficient surface pressure is achieved during its assembly or while the connector link is established, whereby the desired sealing effect is achieved. Accordingly, such circumference grooves usually have somewhat larger dimensions than the seal element itself. As a result of the dead spaces that form in the assembled state of the seal element, the fluid usually flows poorly through or around the area of these seals, which leads to an increase in the formation of germs and an increase in the accumulation of deposits in these areas.

Document CN 202 834 069 U describes a device with a separate disinfection channel within a cylinder housing, in which a pinion is received. This ensures that the flow around the internal components of the device is sufficient and that deposits can be removed easily. This disinfection channel is connected to an external fluid source.

Furthermore, EP 1 574 774 B1 discloses a sealing arrangement with a sealing ring, which is arranged within a groove. Inside the groove or on one flank side of the groove, an indentation is arranged which is connected to the environment via a fluid passage to an opening. Thus, fluid unintentionally accumulated within the groove can be discharged from the sealing ring and can be discharged to the environment via the opening.

Accordingly, various designs of connector elements with a seal free of dead spaces are known from the prior art, but these either require additional fluid sources for cleaning the (internal) components or do not ensure a sufficient supply of fluid to seal elements, especially in connector links.

SUMMARY

The objects and objectives of the disclosure are to overcome or at least reduce the disadvantages of the prior art, and in particular to provide a medical connector link improved over the prior art having a radial seal element around which, in a preferred manner, a fluid sufficiently flows or can flow during operation.

Accordingly, the present disclosure relates to a medical connector link or a system of at least two matching connectors for establishing a fluid connection between two fluid lines. The connector link comprises a first male link element/connector element arranged or arrangeable in a second female link element/connector element such that a fluid passage of the first link element and a fluid passage of the second link element form a common fluid passage. The connector link further comprises a sealing element/seal element, which is arranged within a circumferential groove on an outer side of the first link element or on an inner side of the second link element and seals a radial gap between the second link element and the first link element. The first link element and/or the second link element have at least one recess that fluidically connects the common fluid passage with the circumferential groove or fluidically couples it to each other.

In other words, a medical pinion-cylinder system comprises a cylinder housing, a pinion which is lockably arranged or arrangeable in the cylinder housing such that a fluid passage of the pinion and a fluid passage of the cylinder housing form a common fluid passage for establishing a fluid connection, and the sealing element/seal element. In particular, the pinion-cylinder system is the connector link comprising a male plug and a female jack. Male in this context means that the plug/first link element is convex. The female link element/female jack is essentially concave. The plug is inserted into the jack and locked in the jack. The fluid-tight connector link of the two link elements allows, for example, two fluid lines to be connected to each other. Preferably, the first link element can be locked/fastened in the second link element in such a way that a fluid-tight connection is created between the link elements.

In other words, the seal element is arranged in the medical connector link in order to seal a radial gap between the first and male link element and the second and female link element. This seal element is provided either in a radial groove along the circumference of the first link element or in a radial groove on sides of the second link element, in particular at/on its inner lateral surface. In addition, at least one recess/bore/notch/clearance is arranged or provided on the first link element and/or on the second link element in such a way that the fluid flows around/through/streams through an area of the circumferential groove and the seal element sufficiently or in an improved manner.

When fluid flows through the common fluid passage, the fluid can flow through the at least one recess to the circumferential groove and the seal element. Thus, while a pinion-cylinder connection is established or while a (fluid-tight) connector link is established, the fluid reaches the seal element via the at least one recess or can be discharged from it more easily, whereby the seal element as well as the circumferential groove are better flushed by the fluid. In yet other words, the at least one recess enables a better flow of the fluid/medium in the area of the seal element, which is formed, for example, as an O-ring or a four-lip seal ring, in particular a radial rod seal or pinion seal. With the aid of the minimal dead space construction, the dead space in the area of the seal element is decreased/reduced and the fluid is better entrained, which reduces the risk of germs forming/accumulating. In addition, a disinfection process can be carried out more easily, especially in the area of the seal element or the circumferential groove.

Advantageous embodiments are explained in more detail below.

Preferably, when the first and second link elements are plugged together or when the two link elements are connected, the first link element/pinion can displace a fluid due to an axial displacement in the second link element/cylinder housing. Thus, a displacement space can form between a front face of the first link element and a stop surface of the second link element. Through the at least one recess in the first link element and/or in the second link element, the displacement space can be fluidically connected or fluidically coupled to the circumferential groove.

In another preferred aspect of the disclosure, the at least one recess extends in an axial direction of the first link element. In other words, the at least one recess on the first link element and/or on the second link element is aligned/arranged in an axial direction of the first link element/along the axial axis of the first link element such that the fluid can flow from the fluid passage into the circumferential groove and thus to the seal element when a (connector) link is established between the first link element and the second link element. At the same time, the fluid can flow out of the circumferential groove in the axial direction of the first link element. Due to such an axial alignment of the at least one recess, an inflow or outflow of the fluid to/from the seal element in axial direction is achievable.

It is also conceivable that the recess is formed at an angle to the axial direction of the first link element.

In a first preferred embodiment of the disclosure, the at least one recess is arranged at a first end portion/end piece of the first link element facing the second link element when the connector link is established/in the connected state, between the circumferential groove and the front face of the first link element.

In other words, in a first preferred embodiment, the seal element is arranged in a radial circumferential groove on the first link element and the at least one recess is formed between this circumferential groove and a front face/end surface of the first end portion facing the second link element. The at least first recess enables a flow around the circumferential groove or around the seal element received therein. This preferred first embodiment is simple and thus cost-effective to manufacture, since the at least one recess can be manufactured by injection molding in the same manufacturing step as the entire first link element. There is no need for (re)machining of the first link element. The first link element together with the at least one recess can thus be manufactured in a single manufacturing step.

In another preferred embodiment of the disclosure, at least one of the recesses is arranged on the first end portion of the first link element facing the second link element, between the circumferential groove and the front face of the first link element, and at least one of the recesses is arranged on the stop surface of the second link element.

In other words, in this second preferred embodiment, recesses are arranged on the first link element and (housing) recesses are arranged on the second link element, which are in communication with each other or overflow into each other in order to create a fluid flow between these recesses. The complementary effect of these recesses on both components of the connector link ensures sufficient flow around the seal element or respectively through the circumferential groove.

In another preferred embodiment of the disclosure, at least one of the recesses is arranged on an inner lateral surface portion of the second link element that surrounds the first end portion facing the second link element, and at least one of the recesses is arranged on the stop surface of the second link element.

In other words, in this third embodiment, recesses are arranged on the second link element, i.e. one or more (housing) recesses on/at the stop surface of the second link element as well as one or more (lateral surface) recesses on an inner lateral surface portion of the second link element which embraces/receives the end portion of the first link element facing the second link element. The recesses on the inner lateral surface portion also extend in the axial direction of the first link element and at the same time communicate with the recesses on the stop surface of the second link element, so that fluid can flow over these recesses to the seal element or to the circumferential groove. In this embodiment, no additional recesses on/at the first link element are necessary. Accordingly, the construction of the first link element can be kept simple.

In another preferred embodiment of the disclosure, at least one of the recesses is arranged on an inner lateral surface portion of the second link element surrounding a first end portion of the first link element facing the second link element, and at least one of the recesses is arranged on the end portion of the first link element.

In other words, in this fourth preferred embodiment, the second link element has one or more (lateral surface) recesses extending in particular in the direction of a longitudinal axis of the first link element on the inner lateral surface portion, which embraces/receives the end portion of the first link element facing the second link element. At the same time, one or more recesses are formed on the end portion facing the second link element, which overflow or run out into the corresponding recess or recesses on the inner lateral surface of the second link element. This fourth embodiment of the connector link also allows flow around/through the seal element or the circumferential groove formed in particular on the second link element.

In another preferred aspect of the disclosure, the first end portion has a smaller outer diameter than a second end portion opposite of the first end portion. Thus, the first end portion may have a smaller outer diameter than the remainder of the first link element. In other words, the outer diameter of the first link element is reduced in an end piece/portion facing the second link element. This provides an additional opportunity to achieve unobstructed fluid flow between the seal element and the fluid passage of the connector link. The fluid is then able to flow past the outer circumference of the corresponding end portion of the first link element and thus also to flow more easily into the adjacent recesses on the first link element and/or on the second link element. The flow around/toward the seal element is also improved/simplified.

In another preferred aspect of the disclosure, the recesses are distributed over the circumference of the first link element and/or over the inner circumference of the second link element, in particular at equal distances from each other.

However, the recesses may also be distributed at irregular intervals around the circumference of the first link element and/or around the inner circumference of the second link element.

In another preferred aspect of the disclosure, the fluid passage has a funnel-shaped opening at the stop surface of the second link element. That is, the opening of the fluid passage inside the second link element expands/widens in a funnel-shaped manner toward the stop surface or toward the front face of the first link element. Hereby, improved distribution/spreading of the fluid into the corresponding recesses at the first link element and/or at the second link element is possible. Accordingly, it is possible to dimension the recesses smaller or shorter.

In another preferred aspect of the disclosure, the first link element has a circumferential chamfer on its front face. In other words, a circumferential chamfer is formed at the transition of the front face of the first link element, which faces the fluid passage or the stop surface of the second link element, to the lateral surface of the first link element. This circumferential chamfer makes it easier for fluid to flow around the first end piece, which facilitates flow to the radial seal element. In other words, the flow diameters of the mating components have circumferential chamfers.

BRIEF DESCRIPTION OF THE DRAWING FIGURES

The disclosure and the technical environment are explained in more detail below with reference to the Figures. It should be noted that the disclosure is not intended to be limited by the embodiments shown. In particular, unless explicitly shown otherwise, it is also possible to extract partial aspects of the facts explained in the figures and combine them with other components and findings from the present description and/or figures. In particular, it should be noted that the figures and especially the proportions shown are only schematic. Identical features are referenced with the same reference signs. Furthermore, it is pointed out that the features of the individual embodiments can be interchanged with each other and can occur in a certain combination.

The disclosure is explained in more detail below with reference to preferred embodiments with the aid of figures. The following is shown:

FIGS. 1A-1C show a schematic isometric side view of a first end portion of a first link element facing a second link element, and schematic longitudinal sectional views of the second link element and the connector link according to a first advantageous embodiment;

FIGS. 2A and 2B show a schematic isometric side view of the first end portion and a schematic longitudinal sectional view of the connector link according to a second advantageous embodiment;

FIGS. 3A-3C show a schematic isometric side view of the first end portion and schematic longitudinal sectional views of the second link element and the connector link according to a third advantageous embodiment;

FIGS. 4A-4C show schematic longitudinal sectional views of the end portion, the second link element and the connector link according to a fourth advantageous embodiment; and FIGS. 5A-5C show schematic longitudinal sectional views of the end portion, the second link element and the connector link according to a final, fifth embodiment.

DETAILED DESCRIPTION

FIG. 1A shows a schematic isometric side view of a first end portion of the first and male link element 1, FIG. 1B shows a schematic longitudinal sectional view of a second and female link element 3, and FIG. 1C shows a schematic longitudinal sectional view of a connector link 5 according to a first embodiment formed from the respective components shown in FIGS. 1A and 1B. The first link element 1 has a fluid passage 6 extending along its axis and, at an end piece of the first link element 1, a radial seal element/sealing ring 8 arranged in a circumferential groove 9 on the first link element 1. A front face 11 of the first link element 1, which forms an end surface perpendicular to the axis of the first link element 1 and into which the fluid passage 6 terminates, furthermore has a plurality of recesses 13 distributed along the circumference of the first link element 1. Furthermore, the recesses 13 are evenly spaced from each other, i.e. have equal distances along the circumference of the first link element. However, embodiments in which the recesses are unevenly spaced, i.e. have different distances along the circumference of the first link element 1, are also quite possible. In the embodiment shown, the recesses 13 are formed in such a way that they open into/end in the circumferential groove 9, in which the seal element 8 is arranged, and at the same time penetrate the wall of the fluid passage 6 in the region of the front side 11. The second link element 3 illustrated in FIGS. 1B and 1C has a hollow-cylindrical portion for receiving the first link element 1, which is bounded by a stop surface 15. Furthermore, a funnel-shaped opening 16 is formed at the stop surface 15, which opens into a fluid passage 7 of the second link element 3. A (fluid) chamber 19 is formed between the front face 11 and the stop surface 15. In particular, FIG. 1C shows the plurality of recesses 13 on the first link element 1, through which the circumferential groove 9 or one side of the seal element 8 is in fluid communication with the fluid chamber 19 and thus the fluid passage 7. Furthermore, the first link element 1 has a circumferential chamfer 21 which forms a transition between the front side 11 and the circumferential side of the first link element 1.

FIG. 2A shows the first link element 1 in a further advantageous embodiment and FIG. 2B shows a second embodiment of the connector link 5 with the first link element 1 from FIG. 2A and the second link element 3 from FIG. 1B. In this second embodiment, the recesses 13 are arranged on the first link element 1 in such a way that they do not penetrate the outer wall of the first link element 1, but rest on the inside of the first link element 1 and only penetrate the inner wall of the fluid passage 6 in the region of the front side 11. The recesses 13 extend axially through the first link element 1 to the circumferential groove 9, in which the seal element 8 is arranged. The circumferential groove 9 including the seal element 8 is thus fluidically connected to the fluid passage 7 of the second link element 3.

FIG. 3A shows a schematic isometric side view of the first end portion of the first link element 1 in a further embodiment, and FIGS. 3B and 3C show a schematic longitudinal sectional view of the second link element 3 and the connector link 5 according to a third advantageous embodiment. The first link element 1 of this embodiment differs from the embodiments described above in that the plurality of recesses 13 do not penetrate the wall of the fluid passage 6 or do not protrude into the fluid passage 6 of the first link element 1. The recesses 13 are arranged in the form of external apertures. This allows fluid to flow from the front side 11 in the direction of the seal element 8 or from the circumferential groove 9. The second link element 3 of this third embodiment also has a plurality of further recesses 131 on its stop surface 15, which start from the fluid passage 7 and extend in the direction of the inner wall of the second link element 3. The connector link 5 according to the third embodiment in FIG. 3C shows that the recesses 11 on the first link element 1 and the recesses 131 on the inner side of the second link element 3 are formed in such a way that the seal element 8 or the circumferential groove 9 on the first link element 1 and the fluid passage 7 are in fluidic communication with each other. Fluid therefore flows via the recesses 11 and 131 to the seal element 8 and away from it.

FIGS. 4A and 4B show a schematic longitudinal sectional view of the first end portion and the second link element 3 of a further embodiment. FIG. 4C shows a schematic longitudinal sectional view of the connector link 5 according to a fourth advantageous embodiment, which is composed of the components shown in FIGS. 4A and 4B. The radial seal element 8 is arranged on the inner side of the second link element 3 in the form of a rod seal. In this embodiment, only the second link element 3 has recesses 131 and 132. As in the embodiment of FIGS. 3B and 3C, the recesses 131 are arranged on the stop surface 15, and the recesses 132 are arranged on the inner lateral surface of the second link element 3, which surrounds the first link element 1 in the operating state. The recesses 131, 132 are formed in such a way that they are adjacent to each other and overlap/run into each other. This creates the fluidic connection between the seal element 8 and the fluid passage 7.

FIGS. 5A and 5B show schematic longitudinal sectional views of the first end portion of the first link element 1 and the second link element 3 of a further embodiment. FIG. 5C shows a schematic longitudinal sectional view of the connector link 5 according to a last, fifth embodiment, which is composed of the components shown in FIGS. 5A and 5B. The seal element 8 is arranged on the inner side of the second link element 3, in the form of a rod seal, as in the embodiment shown in FIG. 4B, and the first link element 1 has recesses 13 according to the embodiment shown in FIG. 1A. On the side of the second link element 3, only recesses 132 are arranged on the inner lateral surface of the cylinder housing 3. The formation of the recesses 13 on the first link element 1 enables a fluidic connection between the fluid passage 7 and the seal element 8, since the recesses 13 of the first link element 1 are adjacent to the recesses 132 of the second link element 3. In addition, the fluid passage 7 of the cylinder housing 3 has a funnel-shaped opening 16.

The invention claimed is:

1. A medical connector link for establishing a fluid connection between two fluid lines, the medical connector link comprising:
a first link element having a front face;
a second link element having a stop surface; and
a seal element,
the medical connector link comprising a circumferential groove on an outer side of the first link element or on an inner side of the second link element,
the first link element being arranged or arrangeable in the second link element in an assembled state with the front face of the first link element facing the stop surface of the second link element, such that a fluid passage of the first link element and a fluid passage of the second link element form a common fluid passage extending along an axial direction,
the first link element and the second link element forming a radial gap between the first link element and the second link element,
the seal element being arranged within the circumferential groove,
the seal element sealing the radial gap between the second link element and the first link element, and
the first link element and/or the second link element having at least one recess that fluidically connects the common fluid passage with the circumferential groove when the first link element and the second link element are in the assembled state, wherein the at least one recess comprises:
a first portion that extends, starting from the common fluid passage and extending outward from a center of the common fluid passage, in a direction perpendicular to the axial direction, and
a second portion that extends parallel to the axial direction from the front face of the first link element to the circumferential groove.

2. The medical connector link according to claim 1, wherein a first end portion of the first link element located within the second link element has a smaller outer diameter than a second end portion of the first link element opposite the first end portion.

3. The medical connector link according to claim 1, wherein the first portion of the at least one recess comprises a radial slot formed in the front face of the first link element.

4. The medical connector link according to claim 1, wherein the second portion of the at least one recess extends within an outer circumferential wall of the first link element.

5. The medical connector link according to claim 1, wherein the fluid passage has a funnel-shaped opening at the stop surface of the second link element.

6. The medical connector link according to claim 1, wherein the first portion of the at least one recess comprises a radial slot formed in the stop surface of the second link element.

7. The medical connector link according to claim 1, wherein the second portion of the at least one recess extends within an inner lateral surface portion of the second link element that surrounds a first end portion of the first link element located within the second link element, and the first portion of the at least one recess comprises a radial slot formed in the stop surface of the second link element.

8. The medical connector link according to claim 1, wherein the second portion of the at least one recess extends within an inner lateral surface portion of the second link element that surrounds a first end portion of the first link element located within the second link element, and the first portion of the at least one recess comprises a radial slot formed in the front face of the first link element.

9. The medical connector link according to claim 1, wherein the at least one recess comprises a plurality of recesses that are distributed over an outer circumference of the first link element and/or over an inner circumference of the second link element.

10. The medical connector link according to claim 9, wherein the plurality of recesses are distributed at equal distances from each other.

11. The medical connector link according to claim 1, wherein the first link element has a circumferential chamfer on the front face of the first link element.

12. The medical connector link according to claim 1, wherein the first portion of the at least one recess comprises a radial slot formed in the front face of the first link element, and the second portion of the at least one recess extends within an outer circumferential wall of the first link element.

13. The medical connector link according to claim 1, wherein the first portion of the at least one recess is defined by a radial slot formed in the stop surface of the second link element, and the second portion of the at least one recess extends within an outer circumferential wall of the first link element.

14. The medical connector link according to claim 1, wherein the front face of the first link element contacts the stop surface of the second link element when the first link element and the second link element are in the assembled state.

15. A medical connector link for establishing a fluid connection between two fluid lines, the medical connector link comprising:

a first link element having an outer wall, a front face, and a first fluid passage extending to the front face;

a second link element having an inner wall, a stop surface, and a second fluid passage extending to the stop surface;

a circumferential groove extending into the outer wall of the first link element or the inner wall of the second link element; and a seal element located in the circumferential groove;

wherein the first link element and the second link element are configurable into an assembled state in which:

the inner wall of the second link element surrounds the outer wall of the first link element with a radial gap between the outer wall of the first link element and the inner wall of the second link element, the front face of the first link element is adjacent to the stop surface of the second link element, the seal element seals the radial gap, and the first fluid passage and the second fluid passage extend along a central axis to form a common fluid passage; and wherein the medical connector link further comprises at least one recess defining a fluid pathway that extends starting from the common fluid passage in a direction away from the central axis, and parallel to the central axis from the stop surface of the first link element to the circumferential groove, to thereby form a fluid connection between the common fluid passage and the circumferential groove.

\* \* \* \* \*